United States Patent [19]
Hayashizaki et al.

[11] Patent Number: 6,074,824
[45] Date of Patent: Jun. 13, 2000

[54] METHOD FOR DETERMINING DNA NUCLEOTIDE SEQUENCE

[75] Inventors: Yoshihide Hayashizaki; Nobuya Sasaki, both of Ibaraki, Japan

[73] Assignee: The Institute of Physical and Chemical Research, Saitama, Japan

[21] Appl. No.: 08/836,479

[22] PCT Filed: Nov. 6, 1995

[86] PCT No.: PCT/JP95/02254

§ 371 Date: May 5, 1997

§ 102(e) Date: May 5, 1997

[87] PCT Pub. No.: WO96/14434

PCT Pub. Date: May 17, 1996

[30] Foreign Application Priority Data

Nov. 7, 1994 [JP] Japan .................................. 6-272044

[51] Int. Cl.$^7$ ...................................... C12Q 1/68
[52] U.S. Cl. ...................... 435/6; 435/91.1; 435/91.2; 435/91.5; 435/91.51; 536/24.33; 935/6; 935/8; 935/17; 935/77; 935/78
[58] Field of Search .................. 435/6, 91.1, 91.2, 435/91.5, 91.51; 536/24.33; 935/6, 8, 17, 77, 78

[56] References Cited

U.S. PATENT DOCUMENTS 5,547,835 8/1996 Köster .......................................... 435/6
5,912,118 6/1999 Ansorge et al. .

FOREIGN PATENT DOCUMENTS 42 14 112  2/1993  Germany .

OTHER PUBLICATIONS

Prober et al Science 238:336–341, Oct. 16, 1987.
Kovach et al. J. Natl. Cancer Inst. 83:1004–1009, Jul. 17, 1991.
Axelrod et al. Biochemistry 24:5716–5723, 1985.
Kramer et al. P.N.A.S, USA 75:5334–5338, Nov. 1978.
Klement et al. Gene Analysis Techniques 3:59–66, Jul. 1986.
Copy of European Search Report.

*Primary Examiner*—Kenneth R. Horlick
*Assistant Examiner*—Janell E. Taylor
*Attorney, Agent, or Firm*—Burns, Doane, Swecker & Mathis, L.L.P.

[57] ABSTRACT

Disclosed is a method for determining a nucleotide sequence of DNA product amplified by polymerase chain reaction not requiring removal of primers and/or 2'-deoxyribonucleoside-5'-triphosphates and/or derivatives thereof, which comprises reacting ribonucleoside-5'-triphosphates comprising ATP, GTP, CTP, UTP and derivatives thereof and one or more of 3'-deoxyribonucleotide-5'-triphosphates comprising 3'-dATP, 3'-dGTP, 3'-dCTP, 3'-dUTP and derivatives thereof in the presence of an RNA polymerase and a DNA product which has been amplified by polymerase chain reaction and contains a promoter sequence for the RNA polymerase to afford a nucleic acid transcription product, separating the obtained nucleic acid transcription product and determining a nucleic acid sequence from the resluting separated fractions.

12 Claims, 2 Drawing Sheets

6,074,824

METHOD FOR DETERMINING DNA NUCLEOTIDE SEQUENCE

TECHNICAL FIELD

The present invention relates to a method for determining nucleotide sequence of DNA. More precisely, the present invention relates to a method for determining DNA nucleotide sequence by a direct transcript sequencing method utilizing PCR technique.

BACKGROUND OF THE ART

Because of high performance of polymerase chain reaction (PCR), its applied fields have been expanded year by year (Randall K,. Saiki et al. (1988) Science 239, 487–491). Even a DNA fragment of one molecule can be amplified by the PCR. A direct sequencing method, which is one for sequencing a product amplified by the PCR, is also useful (Corinne Wong et al. (1988) Nature, 330, 384–386). This method enables to reveal information concerning sequence of numerous samples quickly and simultaneously without preparation of libraries and screening thereof.

The direct sequencing method, however, suffers from two serious problems.

First, primers and 2'-deoxyribonucleoside-5'-triphosphates (2'-dNTPs) which have not incorporated remain in reaction systems and interfere the sequencing reaction. Accordingly, the residual primers and 2'-dNTPs must be removed from the PCR products before sequencing in conventional methods. Various kinds of methods for purification of the PCR products are known and which include purification by electrophoresis, ethanol precipitation, filtration, HPLC and the like (see, for example, Dorit R. L. et al. (1991) Current Protocols in Molecular Biology, Vol .II, John Wiley and Sons, New York, 15.2.1–15.2.11). However, all of these methods are complicated.

Second problem is the quick renaturation of PCR products. When the PCR products are renatured into a double-stranded DNA, they are no longer a single-stranded template and interfere the annealing between primers and single-stranded templates. For minimizing the renaturation, there have been proposed, for example, quenching after the denaturation, biotilation of one primer and adsorption of PCR products onto a streptavidin coated surface, use of exonuclease, asymmetric PCR and the like (see, for example, Barbara Bachmann et al. (1990) Nucleic Acid Res. Vol. 18, 1309). However, most of these methods are time-consuming and complicated.

Therefore, an object of the present invention is to provide a completely novel method for determining DNA nucleotide sequence, which does not require to remove the primers and 2'-deoxyribonucleoside-5'-triphosphates (2'-dNTPs) unreacted and remained in PCR reaction systems and which also does not require denaturation so that the problem of quick renaturation of PCR products could be obviated.

SUMMARY OF THE INVENTION

The present invention relates to a method for determining nucleotide sequence of DNA product amplified by polymerase chain reaction, which does not require to remove primers and/or 2'-deoxyribonucleoside-5'-triphosphates and/or derivatives thereof, which comprises reacting ribonucleoside-5'-triphosphates comprising ATP, GTP, CTP, UTP and derivatives thereof and one or more of 3'-deoxyribonucleotide-5'-triphosphates comprising 3'-dATP, 3'-dGTP, 3'-dCTP, 3'-dUTP and derivatives thereof (3'-dNTP derivatives) in the presence of an RNA polymerase and a DNA product which has been amplified by polymerase chain reaction and contains promoter sequence for the RNA polymerase to obtain a nucleic acid transcription product, separating the obtained nucleic acid transcription product and determining nucleic acid sequence from the resulting separated fractions.

The present invention solves the above-mentioned problems in the direct sequence methods and relates to a direct transcript sequencing method utilizing an RNA polymerase such as T7 RNA polymerase and a terminator of RNA transcription reaction (for example, 3'-deoxyribonucleoside-5'-phosphate (3'-dNTPs)).

DISCLOSURE OF THE INVENTION

Figure 1:
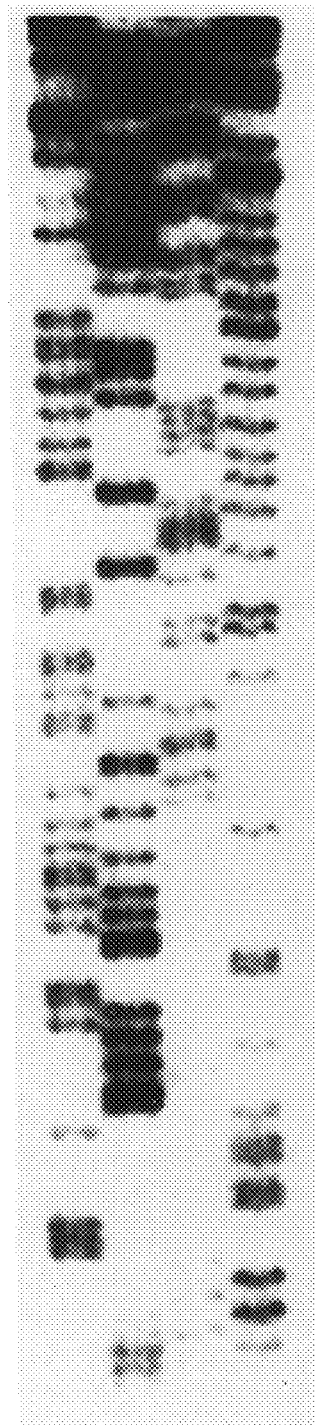
FIG. 1 is a photography of the electrophoresis gel showing the results of autoradiography by the direct transcript sequencing method obtained in Example 1.

The method of the present invention is one for determining nucleotide sequence of DNA product amplified by polymerase chain reaction without removing primers and/or 2'-deoxyribonucleoside-5'-triphosphates and/or derivatives thereof for the polymerase chain reaction.

The DNA polymerase chain reaction used for the present invention may be one of those widely used as PCR methods. Therefore, the DNA sequence which is the object of the amplification, primers, conditions for amplification and the like are not particularly limited.

For example, the reaction is conducted using a DNA polymerase such as Taq polymerase in a 20 μl volume of reaction system containing 10–50 ng of genomic DNA or 1 pg of cloned DNA, 10 μM of each primer, 200 μM of each 2'-deoxyribonucleoside-5'-triphosphate (dATP, dGTP, dCTP, dTTP).

However, either one of the primers for the polymerase chain reaction, or an insert DNA amplified must contain a promoter sequence for RNA polymerase, which will be described hereinafter.

The promoter sequence for the RNA polymerase can be appropriately selected depending on the RNA polymerase to be used.

In the method of the present invention, a nucleic acid transcript such as RNA transcript is synthesized from the DNA product amplified by the polymerase chain reaction. As described above, the DNA product obtained by the amplification contains a promoter sequence for RNA polymerase. Accordingly, this promoter sequence drives RNA polymerase to start synthesis of nucleic acid transcript such as RNA transcripts.

Examples of the RNA polymerase used for the synthesis of nucleic acid transcripts such as RNA transcripts include bacteriophage RNA polymerases (T7, T3, SP6 etc.). Bacteriophage RNA polymerases are widely used for in vitro syntheses of RNA transcripts from cloned DNA templates. These phage RNA polymerases specifically transcript DNA sequences downstream from their promoters (P. A. Krieg et al. (1987) Methods in Enzymology 155, 397–415).

For syntheses of nucleic acid transcripts such as RNA transcripts, one or more of ribonucleoside-5'-triphosphates (NTPs) including ATP, GTP, CTP, UTP and derivatives thereof and one or more 3'-dNTP derivatives are reacted in the presence of the RNA polymerase. The term "3'-dNTP derivative" is used herein as a generic term for indicating 3'-dATP, 3'-dGTP, 3'-dCTP, 3'-dUTP and derivatives thereof. As the ribonucleoside-5'-triphosphates (NTPs), including the case where a part of them is constituted with derivatives such as ATP, at least four kinds of compounds each having a different basic group are necessary for syntheses of transcripts. However, two or more kinds of compounds having the same basic group may be used.

When a 3'-dNTP derivative is incorporated into the 3'-end of the transcription product such as RNA or nucleic acid, the synthesis of RNA or nucleic acid is interfered due to a lack of the 3'-hydroxy group. As a result, RNAs or nucleic acid fragments of various lengths in which a 3'-dNTP derivative has been incorporated into their 3'-ends are generated. With respect to each of four kinds of 3'-dNTP derivatives having a different base, such ribonucleoside analogs are produced. By preparing these four kinds of ribonucleoside analogs, they can be used for determination of RNA or nucleic acid sequence (Vladimir D. Axelred et al. (1985) Biochemistry Vol. 24, 5716–5723).

For one nucleic acid transcription reaction, one or more kinds of the 3'-dNTP derivatives can be used. When one kind of 3'-dNTP derivative is used for one nucleic acid transcription reaction, four kinds of transcription products each having a different base of 3'-dNTP derivative at the 3'-end are obtained by carrying out nucleic acid transcription reaction four times. Through one nucleic acid transcription reaction, a transcription product comprising a mixture of various RNAs or nucleic acid fragments with the same 3'-dNTP derivative at the 3'-end and different molecular weight is obtained. Each of the four transcription products can be independently subjected to separation and sequencing processes described hereinafter. Two or more of the four transcription products can also be mixed and subjected to the separation and sequencing processes.

When two or more kinds of 3'-dNTP derivatives are used for one nucleic acid transcription reaction at the same time, two or more series of the transcription products whose base of the 3'-dNTP derivative at the 3'-end is different will be contained in one reaction product. The products can be subjected to the separation and sequencing processes described hereinafter. Two or more kinds of the 3'-dNTP derivatives can preferably be used for the nucleic acid transcription reaction at same time to reduce the number of the nucleic acid transcription reaction to be performed.

As described above, in the direct transcript sequence method of the present invention, by using primers either of two kinds of which has a phage promoter sequence in the PCR or using an amplified insert DNA having a phage promoter sequence, the PCR product obtained can be subjected to in vitro transcription utilizing an RNA polymerase driven by the promoter.

Further, transcription of nucleic acid such as RNA is carried out by RNA polymerase in the presence of four kinds of ribonucleoside-5'-triphosphates each having a different base and terminated with 3'-dNTP derivatives. As a result, for each base, a RNA or nucleic acid ladder is formed for sequencing.

In the method of the present invention, the RNA or nucleic acid transcription product is separated. The separation can be suitably performed by any method which enables to separate numerous product molecules with different molecular weights contained in the transcription product according to the molecular weight. Examples of such methods include electrophoresis. HPLC can also be used.

Conditions of electrophoresis and the like are not particularly limited and it can be carried out in a conventional manner. Sequence of RNA or nucleic acid can be determined from bands (RNA or nucleic acid ladder) provided by subjecting the transcription product to electrophoresis.

The RNA or nucleic acid ladder can be determined by labeling the ribonucleoside-5'-triphosphates (NTPs) used for the transcription reaction. The RNA or nucleic acid ladder can also be determined by labeling the 3'-dNTP derivatives used for the transcription reaction. Examples of the label include radioactive or stable isotopes, fluorescent labels and the like. 3'-dNTP derivatives labeled with a radioactive or stable isotope are commercially available. For example, 3'-dATP [CORDYCEPIN 5'-TRIPHOSPHINE] is available from SIGMA, ST. LOUIS, Mo., USA under a product No. C9137, and from BOEHRINGER MANNHEIM, Mannheim, Germany under a product No.814288. $\alpha$-$^{32}$P-3'-dATP (3'-[$\alpha$-$^{32}$P]-CORDYCEPIN 5'-TRIPHOSPHINE) is available form DU PONT/NEN Research Products, MA, USA under a product No. NEG-026.). 3'-dNTP derivatives labeled with a fluorescent label can be prepared by a method described in, for example, Japanese Patent Unexamined Publication No.63-152364, Japanese Patent Unexamined Publication No. Hei 7-5170, Japanese Patent Unexamined Publication for PCT application No.5-502371 and the like.

Specifically, sequence of the transcription product can be determined, for example, by using labeled 3-'dNTP derivatives, more specifically, labeled 3'-dATP, 3'-dGTP, 3'-dCTP and 3'-dUTP, and detecting radioactive or stable isotope or fluorescence of the bands obtained from electrophoresis of the transcription product. Thus, labeling of 3'-dNTP derivatives provides uniform intensity of radioactivity or fluorescence and makes the sequencing easy. Detection of radioactive or stable isotope or fluorescence of the ladder can be performed, for example, by an apparatus used for conventional DNA sequencing.

Alternatively, sequence of the transcription product can also be determined by using ATP, GTP, CTP and UTP labeled with radioactive or stable isotope or fluorescence and detecting the radioactive or stable isotope or fluorescence of the bands obtained from electrophoresis of the product.

Furthermore, sequence of RNA or nucleic acid can be determined by using 3'-dATP, 3'-dGTP, 3'-dCTP and 3'-dUTP labeled with different fluorescence and detecting four kinds of fluorescence of the bands obtained by electrophoresis in which differently labeled various transcription product fragments having 3'-dATP, 3'-dGTP, 3'-dCTP or 3'-dUTP at their ends in a mixture are separated each other.

In this method, each of the four kinds of 3'-dNTP is labeled with different fluorescence. Thus, by subjecting a mixture of four kinds of transcription products having different 3'-ends to electrophoresis, bands generating fluorescence corresponding to the four different kinds of 3'-dNTP of 3'-end can be obtained and sequences of four kinds of RNAs or nucleic acids can be determined simultaneously by distinguishing the difference of the fluorescence.

DNA sequence used as template of the transcription can be determined from the RNA or nucleic acid sequence determined as above. When a ladder is formed for each base, DNA sequence used as template of the transcription can be determined by integrating RNA or nucleic acid sequence information provided from the four kinds of ladders. When a ladder is formed for two or more bases simultaneously (two or more groups of the base bands are present in the same ladder), DNA sequence used as template of the transcription can be determined by integrating RNA or nucleic acid sequence information provided from each of the ladders. In particular, when a ladder is formed for four kinds of bases simultaneously (four groups of the base bands are present in the same ladder), DNA sequence used as template of the transcription can be determined from RNA or nucleic acid sequence information provided from the single ladder.

According to the method of the present invention, nucleotide sequence of DNA of PCR product can be determined from the PCR product without purification.

This advantage is brought by the characteristic of RNA polymerase that 2'-dNTP remaining in the reaction mixture is not used as reactive agent in the RNA transcription reaction when 3'-dNTPs for the sequencing are present.

Furthermore, the method of the invention does not require use of single-stranded template DNAs and primers, and denaturation for hybridization of the sequencing primer unlike usual DNA sequence methods, because it utilizes transcription reaction of RNA. Therefore, it enables easy sequencing of DNA without influence of renaturation of PCR products.

The present invention will be further explained with reference to the following examples.

EXAMPLE 1

PCR reaction

As a template of PCR reaction, human TSHβ fragment combined to Bluescript II vector was used. Reaction was performed in 20 μl volume containing 1 pg of the above DNA fragment, 10 μM each of primers (T7 primer and M13 reverse primer) and 200 μM of 2'-deoxyribonucleoside-5'-triphosphates (dATP, dGTP, dCTP, dTTP). To this system, Taq polymerase buffer (50 mM KCl, 10 mM Tris-HCl (pH 8.3), 1–3 mM $MgCl_2$, 0.01% gelatin) and 0.5 unit of Taq polymerase were added.

The first cycle was performed at 95° C. for 5 minutes (denaturation), at 55–60° C. for 1 minute (annealing) and at 72° C. for 2 minutes (extension). Then, 25 to 30 cycles were performed at 95° C. for 1 minute, at 55 to 60° C. for 1 minute and at 72° C. for 2 minutes. The final extension step was extended to 10 minutes.

Sequencing reaction 1 to 5 μl of the above PCR product was added to a sampling tube containing 10–50 μM of 3'-dATP, one of 3'-deoxyribonucreotide-5'-triphosphates, 100 μM each of ribonucleoside-5'-triphosphates (ATP, GTP, CTP, UTP), 0.5 μl of α-$^{32}$P-UTP (3000 Ci/mmol, 10 mCi/ml, Amercham, Buckinghamshire, UK), 40 mM of Tris-HCl (pH 7.5), 5 to 10 mM of $MgCl_2$, 10 mM of dithiothreitol and 1–5 units of T7 RNA polymerase in 10 μl total volume.

The above procedure was repeated for each case where 3'-deoxyribonucleotide-5'-triphosphate is 3'-dCTP, 3'-dGTP or 3'-dUTP.

The obtained samples were incubated at 37° C. for 30 minutes. Subsequently, each reaction mixture was mixed with 3 μl of formamide dye (95% formamide, 10 mM EDTA, 0.05% Bromophenol Blue and 0.05% xylenecyanol), heated at 80° C. for 5 minutes and immediately applied to 6% sequencing gel to fill up a lane. Electrophoresis was performed at a constant power of 30 W for two hours. The gel was dried on filter paper and analyzed by BAS2000 image analyser (FUJI).

As a result, a sequence ladder was formed by the above protocol as shown in FIG. 1.

EXAMPLE 2

PCR reaction was performed as Example 1 to obtain a PCR reaction product and sequencing of this PCR reaction product was performed as follows.

1–5 μl of the above PCR reaction product was added to a sampling tube containing 10–50 μM of 3'-dUTP, one of 3'-deoxyribonucreotide-5'-triphosphates, labeled with a fluorescent substance (Tetramethylrhodamine), 100 μM each of ribonucleoside-5'-triphosphates (ATP, CTP, GTP, UTP), 40 mM of Tris-HCl (pH 7.5), 5 to 10 mM of $MgCl_2$, 10 mM of dithiothreitol and 1–5 units of T7 RNA polymerase in 10 μl total volume. The 3'-deoxyribonucreotide-5'-triphosphates labeled with Tetramethyl-rhodamine was prepared as described in the reference example hereinafter.

Figure 2:
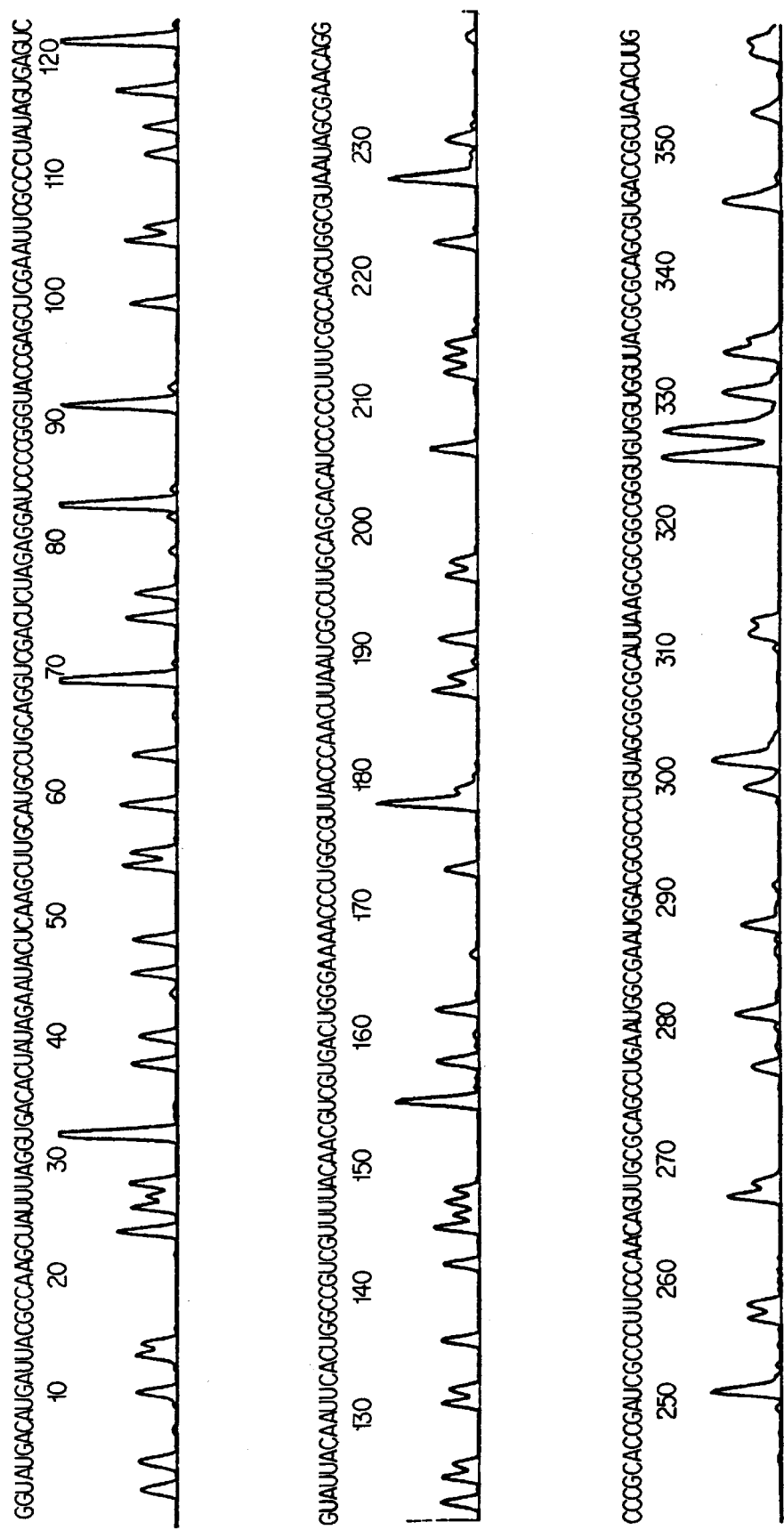
FIG. 2 shows results of electropherogram by the fluorescence direct transcript sequencing method obtained in Example 2.

The obtained sample was incubated at 37° C. for 30 minutes. Subsequently, excessive 3'-dUTP labeled with fluorescence was removed by phenol/chloroform extraction, ethanol precipitation or the like and precipitates were dissolved in 3 μl of formamide dye (95% formamide, 10 mM EDTA), heated at 80° C. for 5 minutes and immediately applied to 4% sequencing gel. Electrophoresis was performed by ABI377 fluorescence automatic sequencer for 7 hours. As a result, electropherogram of U was formed by the above protocol as shown in FIG. 2.

The above procedure can be similarly performed for the case where the 3'-deoxyribonucleotide-5'-triphosphate labeled with fluorescence is 3'-dCTP, 3'-dGTP or 3'-dATP.

REFERENCE EXAMPLE

Preparation of 3'-deoxyuridine-5'-triphosphates labeled with TMR (Tetramethyl-rhodamine)

1) Synthesis of 3'-deoxy-5'-O-dimethoxytrityluridine

3'-deoxyuridine (4 g), triethylamine (2.46 ml) and N,N'-dimethylaminopyridine (0.76 g) were dissolved in pyridine (100 ml), added with a solution of 4,4'-dimethoxytriphenylmethyl chloride (13.13 g) in methylene chloride (70 ml) and allowed to react at room temperature for 25 hours. After completion of the reaction, the reaction mixture was concentrated under reduced pressure, the obtained residue was extracted with ethyl acetate, and the extract was washed with saturated brine. After drying with anhydrous magnesium sulfate, the ethyl acetate was evaporated and the residue was purified by silica gel column chromatography (eluent: mixed solvent of ethyl acetate/n-hexane) to afford 3'-deoxy-5'-O-dimethoxytrityluridine (9.04 g, yield: 97.2%).

2) Synthesis of 2'-O-Acetyl-3'-deoxy-5'-O-dimethoxytrityluridine

3'-deoxy-5'-O-dimethoxytrityluridine (9.02 g) was dissolved in pyridine (100 ml), added with anhydrous acetic acid (30 ml) under ice cooling and allowed to react at room temperature in a single reaction mixture. After completion of the reaction, the reaction mixture was concentrated under reduced pressure, the obtained residue was extracted with ethyl acetate, and the extract was washed with saturated brine. After drying with anhydrous magnesium sulfate, the ethyl acetate layer was evaporated and purified by silica gel column chromatography (eluent: mixed solvent of ethyl acetate/n-hexane) to afford 2'-O-acetyl-3'-deoxy-5'-O-dimethoxytrityluridine (7.12 g, yield: 73.2%).

3) Synthesis of 2'-O-acetyl-3'-deoxyuridine

2'-O-acetyl-3'-deoxy-5'-O-dimethoxytrityluridine (7.12 g) was dissolved in 80% acetic acid and allowed to react at room temperature in a single reaction mixture. After completion of the reaction, the reaction mixture was concentrated under reduced pressure and the obtained residue was purified by silica gel column chromatography (eluent: mixed solvent of ethyl acetate/methanol) and crystallized from ethyl acetate/n-hexane to afford 2'-O-acetyl-3'-deoxyuridine (2.58 g, yield: 76.8%).

Melting point: 148–149° C. $^1$H-NMR (270 MHZ, DMSO-$d_6$) δ ppm: 1.92–2.01 (m, 1H, 3'-Ha), 2.06(s, 3H, $CH_3CO$), 2.17–2.23 (m, 1H, 3'-Hb), 3.35 (brs, 1H, 5'-OH), 3.52, 3.71 (2dd, 2H, J=3.2, 12.2; 2.7, 11.9, 5'-Ha,b), 4.20–4.30 (m, 1H, 4'-H), 5.22–5.26 (m, 1H, 2'-H), 5.61 (dd, 1H, J=2.2, 8.1 Hz, 5-H), 5.78 (d, 1H, J=2.7 Hz, 1'-H), 7.91 (d, 1H, J=8.1 Hz, 6-H), 11.32 (brs, 1H, NH)

4) Synthesis of 2'-O-acetyl-3'-deoxy-5-iodouridine

To a solution of 2'-O-acetyl-3'-deoxyuridine (2.47 g) in acetonitrile (150 ml), diammonium cerium (IV) nitrate (2.51 g) and iodine (1.39 g) were added and allowed to react at 80° C. for one hour. After completion of the reaction, the reaction mixture was concentrated under reduced pressure, the obtained residue w s extracted with ethyl acetate, and the extract was washed with 5% aqueous solution of sodium bisulfite and saturated brine. The ethyl acetate layer was dried with anhydrous magnesium sulfate, and the solvent was evaporated to afford 2'-O-acetyl-3'-deoxy-5'-iodouridine (3.37 g, yield: 93.1%).

$^1$H-NMR (270 MHZ, $CDCl_3$) δ ppm: 2.01–2.07 (m, 1H, 3'-Ha), 2.12 (s, 1H, $CH_3CO$), 2.45–2.49 (m, 1H, 3'-Hb), 3.48–3.50 (m, 1H, 5'-OH), 3.75, 4.09 (2dd, 2H, J=2.7, 12.7; 2.0, 12.4 Hz, 5'-Hab), 4.40–4.50 (m, 1H, 2'-H), 5.79 (d, 1H, J=1.9 Hz, 1'-H), 8.28 (s, 1H, 6-H), 9.50 (brs, 1H, NH)

5) Synthesis of 2'-O-Acetyl-3'-deoxy-5-(3"-trifluoroacetamido-1'-propynyl)uridine To a solution of 2'-O-acetyl-3'-deoxy-5-iodouridine (1.0 g) in DMF (12.6 ml), N-propargyltrifluoroacetamide (0.88 ml), copper (I) iodide (96 mg), bis (triphenylphosphine) palladium (II) chloride (177 mg) and triethylamine (0.7 ml) were added under a nitrogen flow and allowed to react at room temperature for four hours. The residue obtained by concentrating the reaction mixture under reduced pressure was dissolved in a mixture of methylene chloride and methanol (40 ml), added with ion exchange resin AG1x8 (Bio-Rad, $HCO_3$-form, 2 g) and stirred for 30 minutes. After filtration, the filtrate was concentrated and the obtained residue was extracted with ethyl acetate, and the extract was washed with saturated brine. After the ethyl acetate layer was dried with anhydrous magnesium sulfate and the solvent was evaporated, the residue was purified by silica gel column chromatography (eluent: mixed solvent of ethyl acetate/n-hexane) to afford 2'-O-acetyl-3'-deoxy-5-(3"-trifluoroacetamido-1"-propynyl)uridine (405 mg, yield: 38.3%).

$^1$-NMR (270 MHZ, DMSO-$d_6$) δ ppm: 1.89–1.92 (m, 1H, 3'-Ha), 2.06 (s, 3H, $CH_3CO$), 2.17–2.26 (m, 1H, 3'-Hb), 3.40 (brs, 1H, 5'-OH), 3.53, 3.76 (2dd, 2H, J=3.1, 11.9; 2.7, 12.1 Hz, 5'-Hab), 4.22–4.30 (m, 3H, 4'-H, —$CH_2$—), 5.28–5.31 (m, 1H, 2'-H), 5.75 (d, 1H, J=1.9 Hz, 1'-H), 8.34 (s, 1H, 6-H), 10.06 (t, 1H, J-5.4 Hz, $NHCOCF_3$), 11.67 (s, 1H, NH)

6) Synthesis of 5-(3"-amino-1"-propynyl)-3'-deoxyuridine-5'-triphosphate

2'-O-acetyl-3'-deoxy-5-(3"-trifluoroacetamide-1"-propynyl)uridine (42 mg) was dissolved in anhydrous pyridine (2 ml), concentrated to dryness under reduced pressure and dried in a desiccator ($P_2O_5$) for one hour. The product was dissolved in anhydrous pyridine (100 μl) and anhydrous dioxane (300 μl) under a nitrogen flow, added with 1M solution of 2-chloro-4H-1,3,2-benzodioxaphospholine-4-on in dioxane (110 μl), and stirred for ten minutes. To the reaction mixture, 0.5 M solution of bis (tri-n-butylammonium) pyrophosphate in DMF (300 μl) and tri-n-butyl ammonium (100 μl) were added and stirred for ten minutes. Subsequently, 1% iodine solution in pyridine/water (98/2, v/v) was added to the reaction mixture and further stirred for 15 minutes. After completion of the reaction, the reaction mixture was added with 5% aqueous solution of sodium bisulfite and concentrated under reduced pressure. The obtained residue was added with water (10 ml), left for 30 minutes, then added with 25% aqueous ammonia (20 ml) and stirred for two hours. The reaction mixture was concentrated to dryness and the obtained residue was purified by DEAE-Toyopearl ion exchange column chromatography (Tosoh, 1.2×30 cm, eluent: triethylammonium carbonate buffer (pH 7.5), 0.05M→0.5M linear concentration gradient, total volume of 2 liters) to afford 5-(3"-amino-1"-propynyl)-3'-deoxyuridine-5'-triphosphate (51 mg, yield: 55%).

7) Syntheses of TMR-labeled 3'-deoxyuridine-5'-triphosphate

To a solution of 5-(3"-amino-1"-propynyl)-3'-deoxyuridine-5'-triphosphate (10.5 μmol) in 1M triethylammonium carbonate buffer (pH 9.05, 1.2 ml), a solution of 5-carboxytetramethylrhodamine succinimide ester (Molecular Probe, 15 mg) in DMF (0.9 ml) was added and stirred at room temperature as a single reaction mixture. The reaction mixture was diluted with water (30 ml) and purified by DEAE-Toyopearl ion exchange column chromatography (Tosoh, 1.2×30 cm, eluent: triethylammonium carbonate buffer (pH 7.5), 0.05M→0.7M linear concentration gradient, total volume of 2 liters) to afford TMR-labeled 3'-deoxyuridine-5'-triphosphate (7.38 μmol, yield: 70.2%).

We claim:

1. A method for determining a nucleotide sequence of DNA product amplified by polymerase chain reaction not requiring removal of primers and/or 2'-deoxyribonucleoside-5'-triphosphates and/or derivatives thereof, which comprises reacting at least four kinds of ribonucleoside-5'-triphosphates, each containing a different base, comprising ATP, GTP, CTP, UTP and derivatives thereof and one or more 3'-deoxyribonucleoside-5'-triphosphates comprising 3'-dATP, 3'-dGTP, 3'-dCTP, 3'-dUTP and derivatives thereof in the presence of RNA polymerase and a DNA product which has been amplified by polymerase chain reaction and wherein said DNA product contains a promoter sequence for the RNA polymerase such that the RNA polymerase uses said DNA product as a template to obtain a nucleic acid transcription product, separating the obtained nucleic acid transcription product into separated fractions of nucleic acid transcription products and determining the nucleic acid sequence from the separated fractions.

2. The method of claim 1, which uses ATP, GTP, CTP and UTP as ribonucleoside-5'-triphosphates.

3. The method of claim 1, which uses 3'-dATP, 3'-dGTP, 3'-dCTP and 3'-dUTP as 3'-deoxyribonucleotide-5'-triphosphates.

4. The method of claim 1, wherein the nucleic acid transcription reaction is performed independently four times for four kinds of 3'-dNTP derivatives each containing a different base: once with 3'-dATP or a derivative thereof; once with 3'-dGTP or a derivative thereof; once with 3'-dCTP or a derivative thereof; and once with 3'-dUTP or a derivative thereof, to afford four kinds of nucleic acid transcription products each having a different base at their 3' end.

5. The method of claim 4, wherein the four kinds of nucleic acid transcription products each having a different base at their 3'-end are independently separated, or two or more kinds of the nucleic acid transcription products are mixed and separated.

6. The method of claim 1, wherein at least one nucleic acid transcription reaction is performed in the presence of two or more of four kinds of 3'-dNTP derivatives each having a different base, the four kinds of 3'-dNTP derivatives being: (1) 3'-dATP or a derivative thereof; (2) 3'-dGTP or a derivative thereof; (3) 3'-dCTP or a derivative thereof; and (4) 3'-dUTP or a derivative thereof; to simultaneously afford two or more kinds of nucleic acid transcription products each having a different base at their 3' end as a mixture.

7. The method of claim 1, wherein one nucleic acid transcription reaction is performed in the presence of the four kinds 3'-dNTP derivatives each having a different base, the four kinds of 3'-dNTP derivatives being: (1) 3'-dATP or a derivative thereof; (2) 3'-dGTP or a derivative thereof; (3) 3'-dCTP or a derivative thereof; and (4) 3'-dUTP or a derivative thereof; to simultaneously afford four kinds of nucleic acid transcription products each having a different base at their 3'-end as a mixture.

8. The method of claim 1, wherein the separation of the nucleic acid transcription product is performed by electrophoresis.

9. The method of claim 1, wherein the ribonucleoside-5'-triphosphates are labeled and the determination of nucleic acid sequence from the separated fractions is performed by detecting signals from the label.

10. The method of claim 1, wherein the 3'-deoxyribonucleoside-5'-triphosphates are labeled and the determination of nucleic acid sequence from the separated fractions is performed by detecting signals from the label.

11. The method of claim 9, wherein the label is a radioactive or stable isotope or fluorescent label.

12. The method of claim 10, wherein the label is a radioactive or stable isotope or fluorescent label.

* * * * *